US010946384B2

(12) United States Patent
Saito et al.

(10) Patent No.: US 10,946,384 B2
(45) Date of Patent: Mar. 16, 2021

(54) THERMAL CONVECTION GENERATING CHIP, THERMAL CONVECTION GENERATING DEVICE, AND THERMAL CONVECTION GENERATING METHOD

(71) Applicant: OSAKA UNIVERSITY, Osaka (JP)

(72) Inventors: Masato Saito, Suita (JP); Eiichi Tamiya, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 442 days.

(21) Appl. No.: 15/021,087

(22) PCT Filed: Mar. 7, 2014

(86) PCT No.: PCT/JP2014/056002
§ 371 (c)(1),
(2) Date: Mar. 10, 2016

(87) PCT Pub. No.: WO2015/037255
PCT Pub. Date: Mar. 19, 2015

(65) Prior Publication Data
US 2016/0214112 A1  Jul. 28, 2016

(30) Foreign Application Priority Data

Sep. 11, 2013  (JP) .............................. JP2013-188277

(51) Int. Cl.
*B01L 7/00* (2006.01)
*C12Q 1/686* (2018.01)
(Continued)

(52) U.S. Cl.
CPC ........... *B01L 7/525* (2013.01); *B01L 3/50273* (2013.01); *C12P 19/34* (2013.01); *C12Q 1/686* (2013.01);
(Continued)

(58) Field of Classification Search
CPC ....................................................... B01L 7/525
(Continued)

(56) References Cited

U.S. PATENT DOCUMENTS 6,586,233 B2  7/2003 Benett et al.
7,645,581 B2  1/2010 Knapp et al.
(Continued)

FOREIGN PATENT DOCUMENTS

JP  2006-511239 A  4/2006
JP  2006-126010 A  5/2006
(Continued)

OTHER PUBLICATIONS

English written translation of document entitled "Enshin Sokushingata Netsu Tairyu On-chip PCR no Kaihatsu to Oyo" provided by USPTO, Saito et al., May 23, 2013, Society for Chemistry and Micro Nano Systems (Year: 2013).*

(Continued)

*Primary Examiner* — Holly Kipouros
(74) *Attorney, Agent, or Firm* — Studebaker & Brackett PC

(57) ABSTRACT

A thermal convection generating device (1) that generates thermal convection of a liquid by heating or cooling the liquid and applying centrifugal force to the liquid, the thermal convection generating device including: a stage (20) to which a thermal convection generating chip (10) is attachable and detachable, the thermal convection generating chip including a disk-like substrate (11) and a thermal convection pathway (14) formed in a surface of the disk-like substrate that is perpendicular to an axis (AX) of the disk-like substrate, and being configured to rotate about the axis of the disk-like substrate to apply centrifugal force to a liquid in the thermal convection pathway; a heat controller (30) that heats or cools a portion of the thermal convection (Continued)

pathway; a motor (40) that drives the thermal convection generating chip to rotate about the axis; and a controller (50) that controls the heat controller and the motor.

20 Claims, 15 Drawing Sheets

(51) Int. Cl.
*B01L 3/00* (2006.01)
*C12P 19/34* (2006.01)
(52) U.S. Cl.
CPC ... *B01L 2200/06* (2013.01); *B01L 2200/0684* (2013.01); *B01L 2300/0636* (2013.01); *B01L 2300/0803* (2013.01); *B01L 2300/088* (2013.01); *B01L 2300/1805* (2013.01); *B01L 2400/0409* (2013.01); *B01L 2400/0445* (2013.01); *B01L 2400/0688* (2013.01)
(58) Field of Classification Search
USPC .................................................. 435/287.2
See application file for complete search history.

(56) References Cited

U.S. PATENT DOCUMENTS

| | | | |
|---|---|---|---|
| 7,695,685 B2* | 4/2010 | Koide | B01F 13/1022 422/502 |
| 7,919,306 B2 | 4/2011 | Takagi | |
| 7,998,708 B2 | 8/2011 | Handique et al. | |
| 8,088,616 B2 | 1/2012 | Handique | |
| 8,275,554 B2 | 9/2012 | Knapp et al. | |
| 8,697,362 B2 | 4/2014 | Knapp et al. | |
| 8,883,490 B2 | 11/2014 | Handique et al. | |
| 9,040,288 B2 | 5/2015 | Handique et al. | |
| 9,205,426 B2 | 12/2015 | Koeda | |
| 2002/0127152 A1 | 9/2002 | Benett et al. | |
| 2005/0042639 A1 | 2/2005 | Knapp et al. | |
| 2005/0087479 A1* | 4/2005 | Okada | B01L 3/5027 210/94 |
| 2005/0272144 A1* | 12/2005 | Sando | B01F 13/0059 435/287.2 |
| 2006/0091085 A1 | 5/2006 | Kobayashi et al. | |
| 2007/0275426 A1* | 11/2007 | Wo et al. | |
| 2007/0292941 A1 | 12/2007 | Handique et al. | |
| 2008/0085521 A1 | 4/2008 | Knapp et al. | |
| 2008/0090244 A1 | 4/2008 | Knapp et al. | |
| 2008/0131956 A1 | 6/2008 | Chung et al. | |
| 2008/0149840 A1 | 6/2008 | Handique et al. | |
| 2008/0160601 A1 | 7/2008 | Handique | |
| 2008/0182301 A1 | 7/2008 | Handique et al. | |
| 2009/0148912 A1 | 6/2009 | Takagi | |
| 2010/0086990 A1 | 4/2010 | Stanley et al. | |
| 2010/0129896 A1 | 5/2010 | Knapp et al. | |
| 2010/0267127 A1 | 10/2010 | Chung et al. | |
| 2011/0210257 A9 | 9/2011 | Handique et al. | |
| 2011/0256590 A1 | 10/2011 | Koeda | |
| 2012/0288672 A1* | 11/2012 | Ogilvie et al. | |
| 2013/0109022 A1 | 5/2013 | Hwang | |
| 2014/0255933 A1 | 9/2014 | Ozawa et al. | |

FOREIGN PATENT DOCUMENTS

| | | |
|---|---|---|
| JP | 2009-136220 A | 6/2009 |
| JP | 2010-519892 A | 6/2010 |
| JP | 2010-533490 A | 10/2010 |
| JP | 2011-152126 A | 8/2011 |
| JP | 2011-217699 A | 11/2011 |
| JP | 2012-183504 A | 9/2012 |
| JP | 2012-242150 A | 12/2012 |
| JP | 2013-516975 A | 5/2013 |
| JP | 2014-039498 A | 3/2014 |
| WO | 02/072267 A1 | 9/2002 |
| WO | 2011/086497 A2 | 7/2011 |
| WO | 2013/077391 A1 | 5/2013 |

OTHER PUBLICATIONS

Lok et al., "Sample loading and retrieval by centrifugation in a closed-loop PCR microchip," Nov. 30, 2011, Microchim Acta, 176:445-453 (Year: 2011).*
Sundberg et al., "Spinning disk platform for microfluidic digital polymerase chain reaction," Feb. 15, 2010, Analytical Chemistry, vol. 82 No. 4, 1546-1550 (Year: 2010).*
Huang et al., "Surface roughness analysis and improvement of PMMA-based microfluidic chip chambers by CO2 laser cutting," Oct. 6, 2010, Applied Surface Science, 256, 1675-1678 (Year: 2010).*
International Search Report issued in PCT/JP2014/056002; dated Jun. 10, 2014.
The extended European search report issued by the European Patent Office dated Apr. 6, 2017, which corresponds to European Patent Application No. 14844310.4-1371 and is related to U.S. Appl. No. 15/021,087.
An Office Action issued by the Japanese Patent Office dated Jun. 27, 2017, which corresponds to Japanese Patent Application No. 2013-188277 and is related to U.S. Appl. No. 15/021,087.

* cited by examiner

THERMAL CONVECTION GENERATING CHIP, THERMAL CONVECTION GENERATING DEVICE, AND THERMAL CONVECTION GENERATING METHOD

TECHNICAL FIELD

The present invention relates to a thermal convection generating chip, a thermal convection generating device, and a thermal convection generating method that are used for thermal convection PCR and the like.

BACKGROUND ART

Polymerase chain reaction (hereinafter, referred to as PCR) is known as a gene amplification method. The PCR is a method that allows for amplification of a great amount of specific DNA fragments from an extremely small amount of DNA sample in a short time. The method is simple to conduct and therefore is nowadays applied to a wide range of fields from clinical genetic diagnosis to food hygiene inspection and criminal investigation as well as basic research.

Patent Literature 1 discloses a thermal convection PCR apparatus that performs PCR by generating thermal convection in an upright cylindrical container through supply of heat from a bottom side of the container. The thermal convection PCR apparatus is to drive a solution by convection and is advantageous in that PCR solution sending can be performed without the use of an external pump.

Patent Literature 2 discloses a thermal convection PCR apparatus that promotes thermal convection by heating a liquid contained in a cylindrical reaction vessel angled relative to a vertical axis while simultaneously rotating the reaction vessel about the vertical axis and thus applying centrifugal force to the liquid.

CITATION LIST

Patent Literature

[Patent Literature 1]
  WO2002/072267
[Patent Literature 2]
  WO2011/086497

SUMMARY OF INVENTION

Technical Problem

However, the apparatuses disclosed in Patent Literature 1 and Patent Literature 2 are large-sized and therefore need large installation space. It should be noted that a thermal convection generating device that is compact and capable of generating stable thermal convection has been desired also in other fields than the field of PCR.

Solution to Problem

In order to solve the above-mentioned problem, a thermal convection generating chip according to the present invention includes at least one annular thermal convection pathway, wherein the thermal convection generating chip is configured to rotate to apply centrifugal force to a liquid in the thermal convection pathway.

The thermal convection generating chip may include at least one liquid supply path through which a liquid is supplied to the thermal convection pathway.

In this case, the thermal convection generating chip may be configured to rotate to apply centrifugal force to a liquid in the liquid supply path to cause the liquid to move into the thermal convection pathway. Thus, liquid supply to the thermal convection pathway is facilitated and operation is simplified.

Furthermore, the thermal convection generating chip may include at least one gas discharging path configured to receive gas in a liquid in the thermal convection pathway. Thus, gas can be removed from the liquid, enabling smooth thermal convection.

The thermal convection pathway may have a truly circular shape. Thus, the thermal convection pathway can be minimized in length, improving the efficiency of liquid processing.

The thermal convection generating chip may include a plurality of the thermal convection pathways that are rotatable about an axis and that are arranged in a symmetric manner with respect to the axis. Such a configuration allows a plurality of liquids to be processed at the same time, improving processing efficiency.

The thermal convection pathway may have a wall with a surface roughness Ra of no greater than 100 nm. Such a configuration is preferable because formation of air bubbles in the liquid in the thermal convection pathway can be restricted.

The thermal convection pathway may have a wall of a material being any of cyclic olefin, polypropylene, and polycarbonate. Such a configuration is preferable because formation of air bubbles in the liquid in the thermal convection pathway can be restricted.

The fields to which the thermal convection generating chip according to the present invention is applied are not particularly limited. For example, the thermal convection generating chip can be used for performing thermal convection PCR.

A thermal convection generating device according to the present invention includes: a chip mounting section to which a thermal convection generating chip is attachable and detachable, the thermal convection generating chip including at least one thermal convection pathway and being configured to rotate to apply centrifugal force to a liquid in the thermal convection pathway; a heat controller configured to heat or cool a portion of the thermal convection pathway of the thermal convection generating chip; and a driver configured to rotationally drive the thermal convection generating chip.

The heat controller may include a low temperature heat controller and a high temperature heat controller. A difference in temperature between a heating portion of the low temperature heat controller and a heating portion of the high temperature heat controller may be no less than 10° C. A difference in temperature between the heating portion of the low temperature heat controller and a gap between the heating portion of the low temperature heat controller and the heating portion of the high temperature heat controller may be no less than 10° C. A difference in temperature between the gap and the heating portion of the high temperature heat controller may be no less than 10° C. Such a configuration is preferable because thermal convection of the liquid in the thermal convection pathway can be efficiently promoted.

An area of the thermal convection pathway that is opposite to the heat controller may have a temperature higher or lower than an area of the thermal convection pathway other than the area opposite to the heat controller. Such a configuration is preferable because thermal convection of the liquid in the thermal convection pathway can be efficiently promoted.

The thermal convection generating device may include a controller configured to control a temperature of the heat controller for heating or cooling the thermal convection pathway, and a speed and a time of the rotational driving of the thermal convection generating chip by the driver.

The fields to which the thermal convection generating device according to the present invention is applied are not particularly limited. For example, the thermal convection generating device can be used for performing thermal convection PCR.

In this case, the thermal convection generating device may include: an excitation light source configured to irradiate the liquid in the thermal convection pathway with excitation light that excites a fluorochrome contained in the liquid in the thermal convection pathway; a fluorescence detector configured to detect fluorescence emitted by the fluorochrome upon irradiation with the excitation light; and an arithmetic control section configured to calculate an amplification of DNA based on the fluorescence detected by the fluorescence detector. Such a configuration enables real-time PCR and therefore allows quantitative determination of template DNA to be made swiftly.

In this case, the thermal convection generating device may further include a position detector configured to detect a position of the thermal convection pathway during the rotational driving of the thermal convection generating chip; and a light source controller configured to drive the excitation light source based on a result of the detection by the position detector. Such a configuration is preferable because the accuracy of fluorescence detection is improved.

Furthermore, the excitation light source and the fluorescence detector may be configured to rotate integrally with the thermal convection generating chip instead of providing the position detector and the light source controller. Such a configuration is preferable because the accuracy of fluorescence detection is improved and the manufacturing cost is reduced.

A thermal convection generation method according to the present invention includes: a chip preparation step of preparing a thermal convection generating chip including at least one annular thermal convection pathway and being configured to rotate to apply centrifugal force to a liquid in the thermal convection pathway; a liquid supply step of supplying the liquid into the thermal convection pathway; and a thermal convection promotion step of heating or cooling a portion of the thermal convection pathway while rotationally driving the thermal convection generating chip to apply centrifugal force to the liquid.

The liquid in the thermal convection pathway may include an evaporation inhibitor liquid having either or both of a boiling point higher than a maximum temperature of a heat controller configured to heat the liquid and a specific gravity smaller than that of the liquid. Such a method is preferable because evaporation of the liquid is inhibited.

The fields to which the thermal convection generation method according to the present invention is applied are not particularly limited. For example, the thermal convection generation method can be used for performing thermal convection PCR.

In this case, the liquid may include a fluorochrome, and the thermal convection promotion step may include: an excitation light irradiation step of irradiating the liquid in the thermal convection pathway with excitation light that excites the fluorochrome; a fluorescence detection step of detecting fluorescence emitted by the fluorochrome upon irradiation with the excitation light; and an amplification calculation step of calculating an amplification of DNA based on the detected fluorescence. Such a configuration enables real-time PCR and therefore allows quantitative determination of template DNA to be made swiftly.

Advantageous Effects of Invention

The present invention can provide a thermal convection generating device that does not need an external pump and is therefore compact.

DESCRIPTION OF EMBODIMENTS

Hereinafter, embodiments of the present invention will be described with reference to the accompanying drawings. However, the present invention is not limited to the following embodiments.

Figure 1:
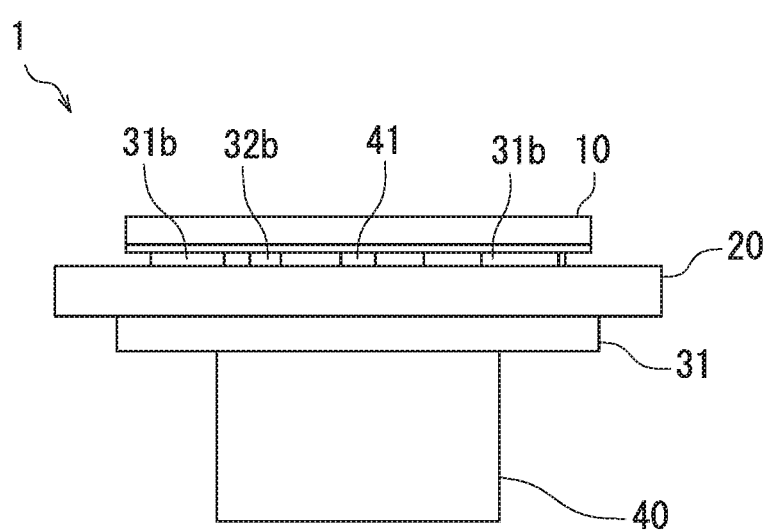
FIG. 1 is a side view of a thermal convection generating device according to a first embodiment of the present invention.
Figure 2:
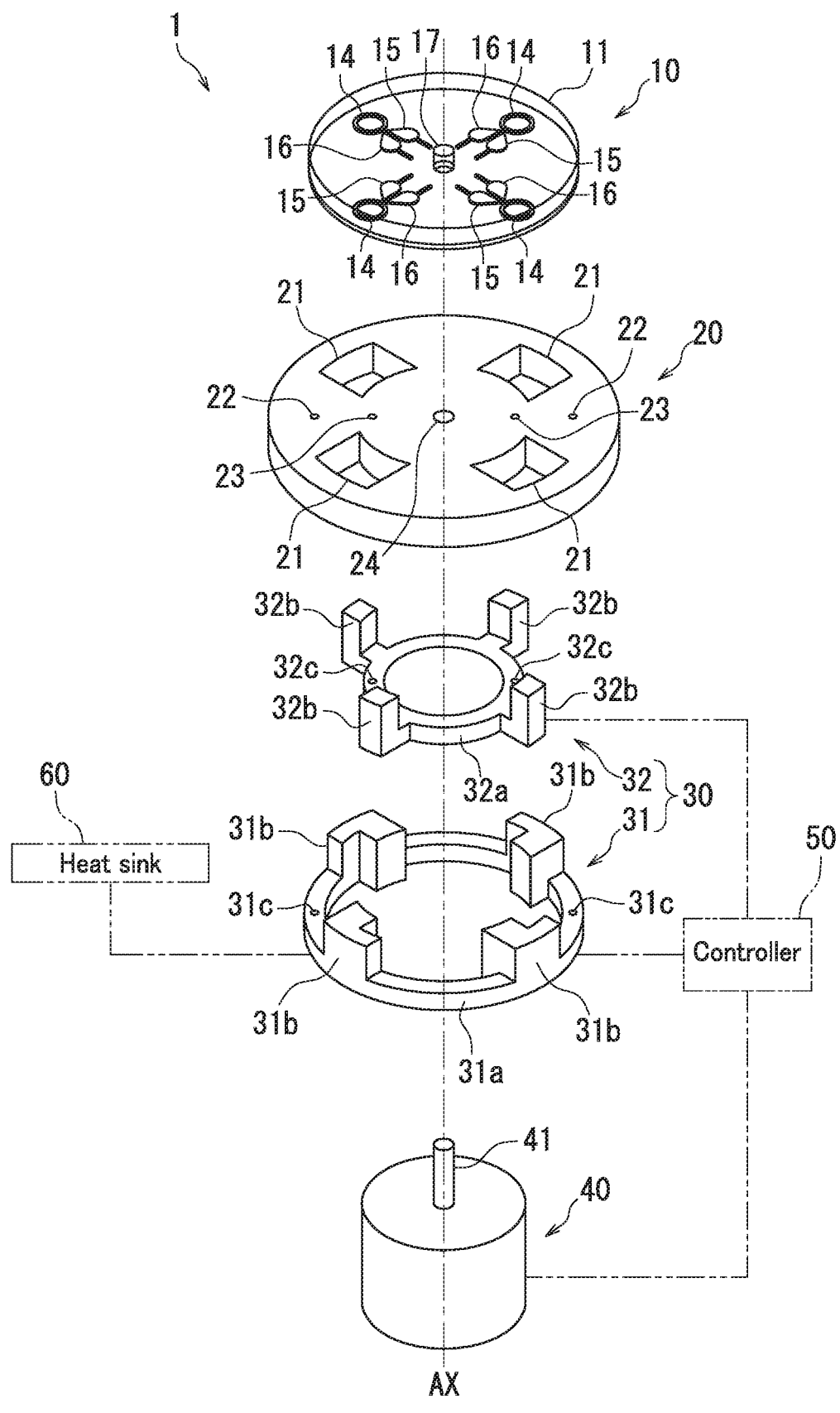
FIG. 2 is an exploded perspective view of the thermal convection generating device according to the first embodiment.

A thermal convection generating device 1 according to a first embodiment of the present invention is a device for performing thermal convection PCR and includes a stage 20 serving as a chip mounting section to which a thermal convection generating chip 10 is attachable and detachable, a heat controller 30, a motor 40, and a controller 50 as illustrated in FIGS. 1 and 2.

Figure 3:
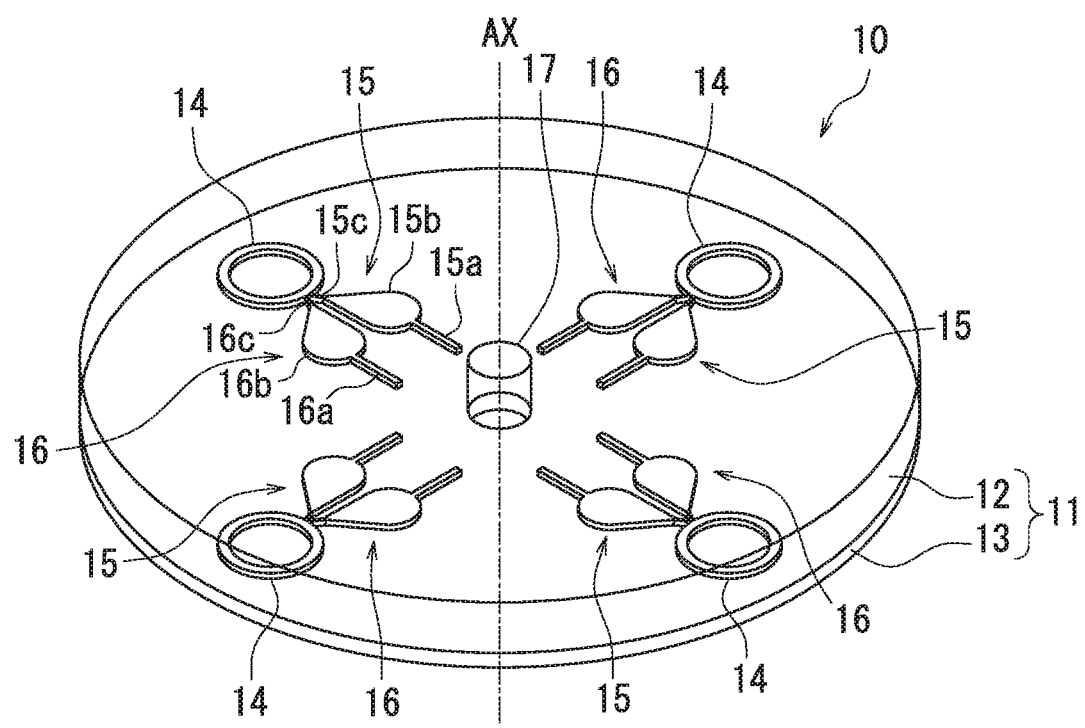
FIG. 3 is an enlarged perspective view of a thermal convection generating chip according to the first embodiment.

As illustrated in FIG. 3, the thermal convection generating chip 10 includes a transparent disk-like substrate 11 that is for example made of a synthetic resin and is in the shape of a disk. The disk-like substrate 11 includes a substrate body 12 and a lid 13 attached to a lower surface of the substrate body 12.

The lower surface of the substrate body 12 has a plurality of thermal convection pathways 14 near a periphery thereof. The thermal convection pathways 14 are arranged about an axis AX of the disk-like substrate 11 at equal angular spacing and in a symmetric manner with respect to the axis AX.

The number, processing method, shape, dimensions, and so forth of the thermal convection pathways 14 are not particularly limited. In the present embodiment, four thermal convection pathways 14 having the same shape and the same size are formed in the substrate body 12 having a diameter of 40 mm by a microfabrication technique, and each thermal convection pathway 14 includes a truly circular groove having a diameter of 5 mm, a groove width of 500 μm, and a depth of 300 μm.

If air bubbles are formed in a liquid in a thermal convection pathway 14, thermal convection therein is inhibited. A design method for the thermal convection pathways 14 for restricting formation of air bubbles in a liquid in each thermal convection pathway 14 will be described later.

Having a truly circular shape, the thermal convection pathways 14 can be minimized in length and allow thermal convection PCR to be carried out swiftly and efficiently. Furthermore, since the thermal convection generating chip 10 includes the plurality of thermal convection pathways 14, a plurality of liquids can be processed at the same time, improving processing efficiency.

A section of each thermal convection pathway 14 that is closest to the axis AX is communicably connected with a liquid supply path 15 and a gas discharging path 16 in a bifurcated manner.

The processing method, shape, dimensions, and so forth of the liquid supply paths 15 and the gas discharging paths 16 are not particularly limited. In the present embodiment, each of the liquid supply paths 15 and a corresponding one of the gas discharging paths 16 are symmetrical to one another and each include a groove formed by a microfabrication technique.

Figure 4:
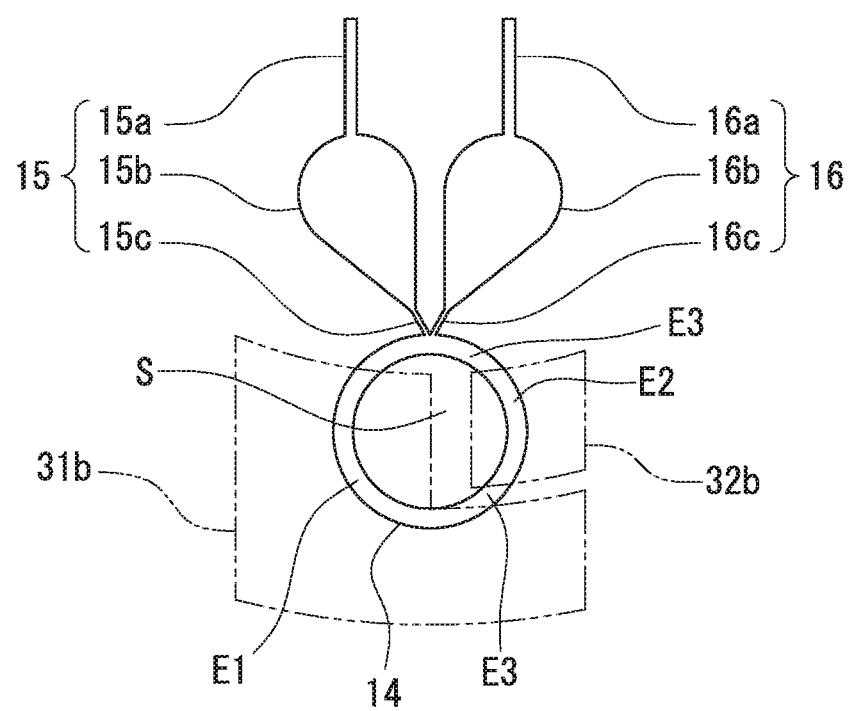
FIG. 4 is an enlarged view of a thermal convection pathway, a liquid supply path, and a gas discharging path according to the first embodiment.

As illustrated in FIG. 4, each liquid supply path 15 has, in order of distance to a corresponding one of the thermal convection pathways 14, a narrow elongated portion 15a extending in a radial direction of the disk-like substrate 11, a teardrop-shaped liquid trap portion 15b communicably connected with one end of the elongated portion 15a, and a communication portion 15c having a small width and communicably connecting a tip of the liquid trap portion 15b with the thermal convection pathway 14. The liquid trap portion 15b has a larger capacity than the thermal convection pathway 14.

Each gas discharging path 16 has, in order of distance to a corresponding one of the thermal convection pathways 14, a narrow elongated portion 16a extending in the radial direction of the disk-like substrate 11, a teardrop-shaped gas trap portion 16b communicably connected with one end of the elongated portion 16a, and a communication portion 16c having a small width and communicably connecting a tip of the gas trap portion 16b with the thermal convection pathway 14.

With the gas discharging path 16, gas generated from a liquid in the thermal convection pathway 14 as a result of thermal convection and gas generated when the liquid is injected into the liquid supply path 15 come into the gas discharging path 16 when subjected to centrifugal force. Thus, gas can be removed from the liquid, enabling smooth thermal convection of the liquid.

The lid 13 (see FIG. 3) has substantially the same diameter as the substrate body 12 and is formed of a disk thinner than the substrate body 12. The lid 13 is attached to the lower surface of the substrate body 12 and detachably fixed to the substrate body 12 with an appropriate fastener.

The stage 20 (see FIG. 2) supports the heat controller 30 and transmits turning force of the motor 40 to the thermal convection generating chip 10. The stage 20 is formed of a disk of a synthetic resin, a metal, or the like.

The stage 20 includes a coupler for coupling the thermal convection generating chip 10 placed on the stage 20 while concentrically aligning the thermal convection generating chip 10 with the stage 20 in a manner non-rotatable with respect to one another. Structure of the coupler is not particularly limited and may for example be a structure in which a recess or a projection formed at a position offset from a central axis of the thermal convection generating chip 10 mates with a projection or a recess formed at a position offset from a central axis of the stage 20.

The stage 20 is provided with four heater mounting holes 21 having an arc shape through which the heat controller 30 is mounted. These heater mounting holes 21 are arranged about the axis AX at 90° angular spacing and in a symmetric manner with respect to the axis AX.

The stage 20 is further provided with a pair of first screw insertion holes 22 through which shafts of screws for fastening a first heater 31 to be described later are inserted and with a pair of second screw insertion holes 23 through which shafts of screws for fastening a second heater 32 to be described later are inserted.

The heat controller 30 includes the first heater 31 having a ring shape, which serves as a low temperature heat controller, and the second heater 32 having a ring shape, which is concentrically disposed at an inner side of the first heater 31 and serves as a high temperature heat controller.

The first heater 31 includes a ring-shaped coupling portion 31a and four columnar heating portions 31b each having an L-shaped horizontal cross section that are arranged at equal spacing in a circumferential direction of the coupling portion 31a.

The coupling portion 31a is provided with a pair of screw holes 31c arranged about the axis AX at 180° angular spacing. The shafts of the screws inserted through the first screw insertion holes 22 of the stage 20 are installed in the screw holes 31c.

Upper ends of the heating portions 31b of the first heater 32 protrude upward from the stage 20 while the first heater 31 is attached to the stage 20 (see FIG. 1).

The second heater 32 includes a ring-shaped coupling portion 32a and four columnar heating portions 32b each having an L-shaped vertical cross section that are arranged at equal spacing in a circumferential direction of the coupling portion 32a.

The coupling portion 32a is provided with a pair of screw holes 32c arranged about the axis AX at 180° angular spacing. The shafts of the screws inserted through the second screw insertion holes 23 of the stage 20 are installed in the screw holes 32c.

Upper ends of the heating portions 32b of the second heater 32 protrude upward from the stage 20 while the second heater 32 is attached to the stage 20 (see FIG. 1).

As illustrated in FIG. 4, each heating portion 31b of the first heater 31 is formed so that an upper surface thereof is opposite to approximately a half of a corresponding one of the thermal convection pathways 14. A heating temperature of each heating portion 31b is approximately 60° C.

On the other hand, each heating portion 32b of the second heater 32 is formed so that an upper surface thereof is opposite to approximately a quarter of a corresponding one of the thermal convection pathways 14. A heating temperature of each heating portion 32b is approximately 95° C.

The heating temperature of each heating portion 31b and the heating temperature of each heating portion 32b are not particularly limited. Preferably, a difference between the heating temperature of each heating portion 31b and the heating temperature of a corresponding one of the heating portions 32b is no less than 10° C. in order to efficiently promote thermal convection. Preferably, a difference between the heating temperature of the heating portion 31b and a temperature of a gap S between the heating portion 31b and the heating portion 32b is preferably no less than 10° C. Preferably, a difference between the temperature of the gap S and the heating temperature of the heating portion 32b is no less than 10° C.

Furthermore, it is preferable that in each thermal convection pathway 14, a temperature of an area E1 opposite to the corresponding heating portion 31b and a temperature of a high temperature area E2 opposite to the corresponding heating portion 32b are higher than a temperature of areas E3 other than the areas E1 and E2. In the case of a heat controller for cooling a liquid in each thermal convection pathway, it is preferable that in the thermal convection pathway, the temperature of the areas opposite to the heat controller is lower than the temperature of the areas other than the areas opposite to the heat controller.

A shaft 41 of the motor 40 is inserted into a center hole 24 of the stage 20 and a center hole 17 of the thermal convection generating chip 10 with the thermal convection generating chip 10, the stage 20, the first heater 31, and the second heater 32 illustrated in FIG. 2 stacked on one another. The shaft 41 of the motor 40 and the stage 20 are fixed together using an appropriate means.

Figure 5:
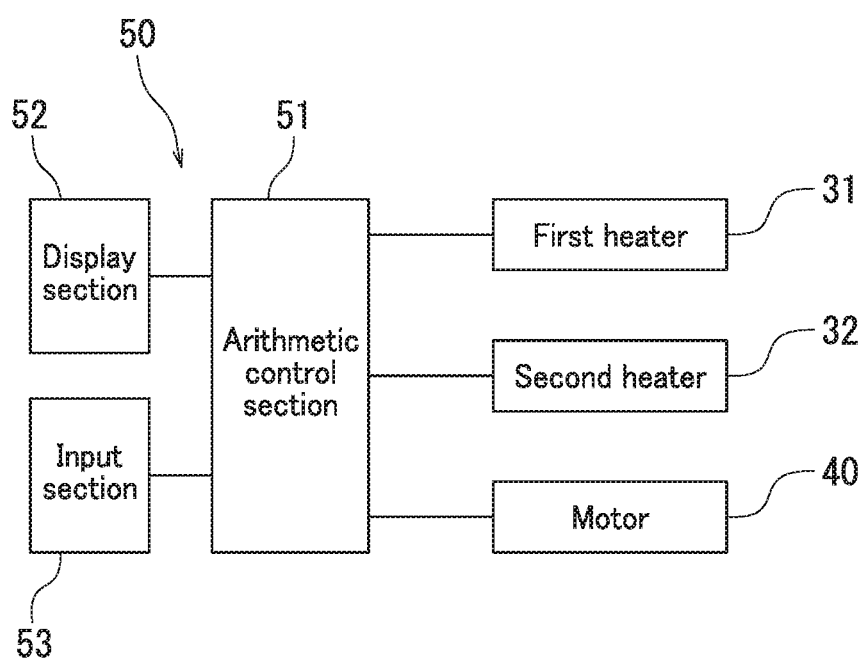
FIG. 5 is a block diagram of a control system according to the first embodiment.

As illustrated in FIG. 5, the controller 50 for controlling the thermal convection generating device 1 includes an arithmetic control section 51, a display section 52, and an input section 53.

The arithmetic control section 51 is composed of a microcomputer including a CPU, ROM, RAM, and the like. The CPU controls the first heater 31, the second heater 32, and the motor 40 in accordance with information input through the input section 53 and a program stored in the ROM. The display section 52 includes a liquid crystal display. The input section 53 includes a keyboard and a mouse.

As indicated by an imaginary line on the left-hand side of FIG. 2, a heat sink 60 for releasing heat generated by the first heater 31 and thus cooling the first heater 31 may be provided. In such a configuration, elimination of excess heat is enabled and the accuracy of thermal convection PCR can be improved at a lower manufacturing cost.

Next, a method for suppressing formation of air bubbles in a liquid in each thermal convection pathway 14 will be described. The following three cases are considered as reasons that air bubbles are formed in a liquid in a thermal convection pathway 14. Case 1: Air bubbles are formed as a result of boiling of the liquid or emergence of gas dissolved in the liquid. Case 2: An area left unwetted when the thermal convection pathway 14 is filled with the liquid turns straight into gas. Case 3: Gas emerges from a material forming the thermal convection pathway 14 or from a material forming the lid 13.

Regarding Case 1, air bubble formation as a result of boiling of the liquid is an unavoidable phenomenon, and basically it is important to control the liquid to be at a temperature no greater than a boiling point thereof. On the other hand, emergence of gas originally dissolved in the liquid can be caused by different reasons as follows and it is possible to take measures against each reason.

In a situation in which air bubbles are formed on or in the liquid due to stirring or the like before the liquid is supplied to the thermal convection pathway 14, most of the air bubbles are eliminated by leaving the liquid to stand in the air for an appropriate period of time. Even if the liquid is supplied to the thermal convection pathway 14 with some air bubbles present therein, the gas can be usually separated or removed from the liquid with a liquid trap portion having an appropriate capacity provided in the thermal convection pathway 14.

Air bubbles may be formed as a result of reduction in solubility of the gas due to a change in either or both of temperature and pressure. Against such a case, it is ideal to vacuum degas the liquid in advance. Even if vacuum degassing is impossible, emergence of the gas can be reduced by increasing an internal pressure of the thermal convection pathway 14. Examples of methods for increasing the inner pressure of the thermal convection pathway 14 include a method involving determining the cross-sectional diameter of the thermal convection pathway 14 and the length of the thermal convection pathway 14 in view of density, flow rate, and pipe friction coefficient of the liquid.

In the present invention, other than the above-mentioned common methods, either or both of formation and growth of the gas from the sample liquid is inhibited by supplying to the thermal convection pathway 14 an evaporation inhibitor liquid having either or both of a boiling point higher than a maximum temperature of the heat controller 30 and a specific gravity smaller than that of the sample liquid so that the evaporation inhibitor liquid precedes and/or follows the sample liquid. Examples of the evaporation inhibitor liquid include mineral oil.

Regarding Case 2, mainly considered are a situation in which the thermal convection pathway 14 is likely to have an unwetted area because of its structure and a situation in which the thermal convection pathway 14 has an unwetted area because the liquid has insufficient wettability for the material forming the pathway of the thermal convection pathway 14.

The former is a situation in which the thermal convection pathway 14 has many acute changes on the way along a traveling direction of the liquid therein such as those in cross-sectional diameter of the pathway and those in the traveling direction. Formation of air bubbles can be restricted by avoiding such a structure as much as possible unless such a structure is intended in order to provide a specific function.

For the latter situation, an unwetted area can be generally reduced by employing a highly hydrophilic material for the material forming the thermal convection pathway 14 and for the material forming the lid 13. Another effective method involves selecting a less hydrophilic material for the material forming the thermal convection pathway 14 or for the material forming the lid 13 and coating portions constituting walls of the thermal convection pathway 14 with a highly hydrophilic material.

It is important to determine the material of the walls of the thermal convection pathway 14 in a comprehensive manner based on advantageous effects and disadvantageous effects of the material in view of Case 3.

Specific examples of the material include cyclic olefin, polypropylene, polycarbonate, complex of polydimethylsiloxane and glass, and acrylic resin.

Of the materials listed above, cyclic olefin is most preferable, and polypropylene and polycarbonate are second most preferable in terms of their high degassing performance and heat resistance, and their low gas permeability, water absorption, and autofluorescence.

In the present embodiment, other than the above-mentioned common method involving material selection, an unwetted area is reduced by polishing the walls of the thermal convection pathway 14 and thus reducing surface roughness thereof to a certain degree. More specifically, the walls of the thermal convection pathway 14 have a surface roughness Ra of no greater than 100 nm, preferably a surface roughness Ra of no greater than 50 nm, and particularly preferably a surface roughness Ra of no greater than 30 nm.

In order to confirm an effect of the polishing, the following test was conducted. First, the thermal convection pathways 14 were formed in the substrate body 12 by cutting, the walls of each thermal convection pathway 14 were coated with polyethylene glycol, the thermal convection pathway 14 was subsequently filled with water containing red food coloring, and the thermal convection generating chip 10 was heated entirely using a heater at 95° C. As a result, formation of air bubbles in the water in the thermal convection pathway 14 was observed in approximately one minute.

Separately, the thermal convection pathways 14 were formed in the substrate body 12 by cutting, the walls of each thermal convection pathway 14 were polished to give a surface roughness Ra of approximately 30 nm, the thermal convection pathway 14 was subsequently filled with water containing red food coloring, and the thermal convection generating chip 10 was heated entirely using a heater at 95° C. As a result, no air bubbles were observed in the water in the thermal convection pathway 14 even after heating for 20 minutes or more.

Figure 6:
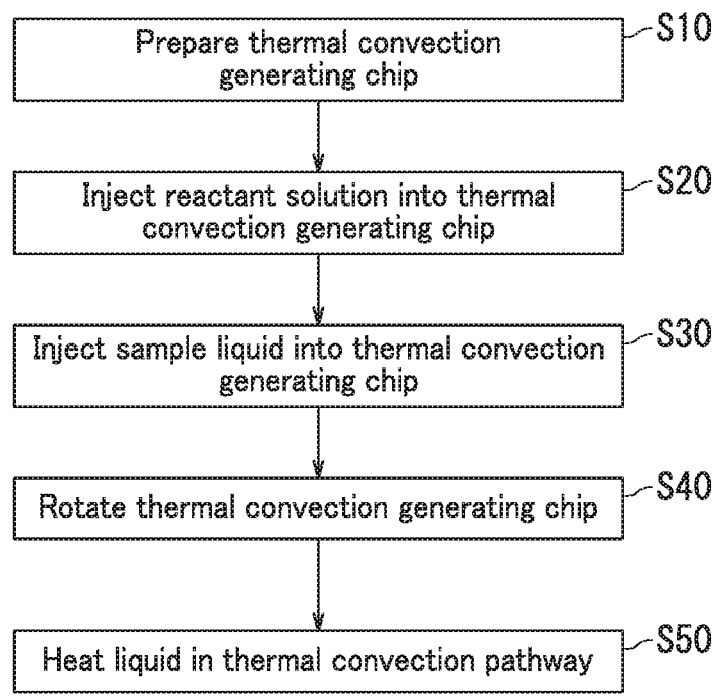
FIG. 6 is a flowchart illustrating a thermal convection generation method using the thermal convection generating device according to the first embodiment.

The following describes a procedure for performing thermal convection PCR using the thermal convection generating device 1 with reference to FIG. 6. FIG. 6 is a flowchart illustrating a method for generating thermal convection using the thermal convection generating device 1.

First, as shown in Step S10, the thermal convection generating chip 10 is prepared. Step S10 corresponds to a chip preparation step according to the present invention.

Next, as shown in Step S20, a reactant solution is injected through an inlet (not shown) formed in a surface of the substrate body 12 of the thermal convection generating chip 10 that is farthest from the lid 13, whereupon the reactant solution flows into the liquid trap portion 15b of a liquid supply path 15 through the elongated portion 15a thereof by capillary action.

Next, as shown in Step S30, a sample liquid such as saliva or blood is injected through the inlet, whereupon the sample liquid flows into the liquid trap portion 15b of the liquid supply path 15 through the elongated portion 15a thereof by capillary action.

Although the reactant solution and the sample liquid flow into the liquid trap portion 15b through the elongated portion 15a by capillary action in the present embodiment, the reactant solution and the sample liquid may be pushed into the liquid trap portion 15b using a pipette or the like.

The reactant solution and the sample liquid that have flowed into the liquid trap portion 15b stay in the liquid trap portion 15b while the thermal convection generating chip 10 is not rotating but move into the corresponding thermal convection pathway 14 through the communication portion 15c by centrifugal force once the thermal convection generating chip 10 starts rotating.

A thin air-tight or liquid-tight resin sheet may be disposed between the substrate body 12 and the lid 13 to provide a sealed closure for the thermal convection pathways 14, the liquid supply paths 15, and the gas discharging paths 16.

An oil that does not hinder PCR may be injected into the liquid supply path 15. In this case, the oil, which has a low specific gravity, accumulates in the liquid trap portion 15b as a result of the rotation of the thermal convection generating chip 10 to function as a lid preventing the liquid in the thermal convection pathway 14 from flowing into the liquid trap portion 15b through the communication portion 15c and prevent the liquid in the thermal convection pathway 14 from evaporating.

Next, the thermal convection generating chip 10, the first heater 31, and the second heater 32 are attached and fixed to the stage 20, and the shaft 41 of the motor 40 is inserted into the center hole 24 of the stage 20 and the center hole 17 of the thermal convection generating chip 10 to fix the stage 20 to the shaft 41.

Next, as shown in Step S40, the stage 20 and the thermal convection generating chip 10 rotate in response to a user operating the input section 53 of the controller 50 to start the motor 40. Furthermore, as shown in Step S50, the first heater 31 and the second heater 32 are energized, and the liquid in the thermal convection generation pathway 14 is heated.

The liquid supply path 15 is located closer to the axis AX of the disk-like substrate 11 than the thermal convection pathway 14. Accordingly, the reactant solution and the sample liquid in the liquid supply path 15 move toward the thermal convection pathway 14 by centrifugal force due to rotation of the thermal convection generating chip 10 and thus move into the thermal convection pathway 14. Step S20 to Step S40 correspond to a liquid supply step according to the present invention.

The reactant solution and the sample liquid in the thermal convection pathway 14 are subjected to thermal convection and mixed together under application of heat and centrifugal force. Step S40 and Step S50 correspond to a thermal convection promotion step according to the present invention.

A reactant solution and a sample liquid may be mixed together to prepare a liquid mixture before being injected into a liquid supply path 15, and the liquid mixture may be injected into the liquid supply path 15 to be subjected to thermal convection in the corresponding thermal convection pathway 14.

In a situation in which the liquid mixture in the thermal convection pathway 14 includes gas, the gas moves toward the axis AX by centrifugal force and flows into the corresponding gas discharging path 16. Thus, the gas in the liquid mixture can be eliminated. As a result, thermal convection of the liquid mixture can be smoothly generated.

The liquid mixture is heated by heat exchange with the corresponding heating portion 32b (approximately 95° C.) of the second heater 32 as it passes over the heating portion 32b. Through the above, a piece of double-stranded DNA in the liquid mixture is separated into two pieces of single-stranded DNA. According to the configuration of the present embodiment, the liquid mixture under thermal convection takes approximately 15 seconds to pass over the heating portion 32b.

Furthermore, the liquid mixture is cooled by heat exchange with the corresponding heating portion 31b (approximately 60° C.) of the first heater 31 as it passes over the heating portion 31b. Through the above, two pieces of single-stranded DNA in the liquid mixture bind to one another into a piece of double-stranded DNA. According to the configuration of the present embodiment, the liquid mixture under thermal convection takes approximately 45 seconds to pass over the heating portion 31b.

The time taken by the liquid mixture under thermal convection to pass over the heating portion 31b of the first heater 31 and the time taken by the liquid mixture under thermal convection to pass over the heating portion 32b of the second heater 32 can be reduced by controlling the rotation speed of the thermal convection generating chip 10, the thermal convection speed of the liquid mixture, or the like.

The drive time of the motor 40 is determined such that heating by the second heater 32 and cooling by the first heater 31 are each performed a specified number of times.

The temperatures of the first heater 31 and the second heater 32, and the speed of the rotational driving of the thermal convection generating chip 10 by the motor 40 can be adjusted through the input section 53 of the controller 50.

The thermal convection generating device 1 according to the present invention does not need an external pump since the device utilizes thermal convection of a liquid. Furthermore, the device is compact since the thermal convection pathways 14 are formed in the disk-like substrate 11. Furthermore, the device can reliably generate heat convection of a liquid since the device applies heat and centrifugal force to the liquid.

Furthermore, since the thermal convection pathways 14 are formed in a surface perpendicular to the axis of the disk-like substrate 11, resultant force in the direction of the rotational axis acting on a liquid being circulated in each thermal convection pathway 14 does not fluctuate. Accordingly, the flow of the liquid is stabilized. Thus, device is highly reliable as being capable of reliably generating stable thermal convection.

Furthermore, the thermal convection pathways 14 can be minimized in pathway length as having a truly circular shape. Besides, the device can process liquids swiftly and efficiently as having the plurality of thermal convection pathways 14.

The following tests were conducted in order to confirm effects of the present invention.

Non-colored water and water colored with red food coloring and the like were injected into a liquid supply path 15 of the thermal convection generating chip 10. First, the inside of the corresponding thermal convection pathway 14 was observed using a high-speed camera with the heat controller 30 not energized. As a result, there was observed no change in darkness or lightness of the liquid in the thermal convection pathway 14 between before and after rotation of the thermal convection generating chip 10 to confirm that only rotating the thermal convection generating chip 10 does not cause the non-colored water and the colored water to be mixed together. The drive time of the motor 40 was 20 seconds, the drive speed thereof was 1,000 rpm, and the value of electric current thereto was 1.4 A.

Next, the inside of the thermal convection pathway 14 before and after rotation of the thermal convection generating chip 10 was observed using a high-speed camera with the heat controller 30 set at a temperature of 50° C. As a result, it was confirmed that thermal convection was generated in the thermal convection pathway 14, and the non-colored water and the colored water were mixed together.

Figure 7:
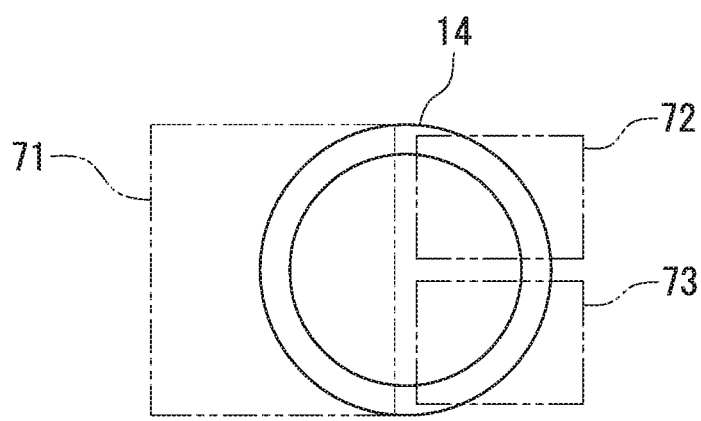
FIG. 7 is a diagram illustrating a test method for confirming an effect of the present invention.

Furthermore, in order to measure the temperature of the thermal convection pathway 14, three adhesive temperature labels 71 (60° C.), 72 (95°), and 73 (100° C.) were placed between a lower surface of the thermal convection generating chip 10 and an upper surface of the corresponding heating portion 31b of the first heater 31, and between the lower surface of the thermal convection generating chip 10 and an upper surface of the corresponding heating portion 32b of the second heater 32 as illustrated in FIG. 7. Temperature indication by the adhesive temperature labels 71 to 73 changes between black, brown, green, blue, and purple in the noted order with increase in temperature.

The thermal convection generating chip 10 was driven to rotate for 10 minutes with a power source connected with the second heater 32 set at a temperature of 115° C. and a DC power source for the motor 40 set at a voltage of 0.5 V. It should be noted that the heater 31 was not energized. No color change was observed in the adhesive temperature label 72 in comparison between colors of the adhesive temperature label 72 before and after rotation of the thermal convection generating chip 10, and it is therefore thought that air-cooling due to the rotation of the thermal convection generating chip 10 had no influence. It was revealed from the color of the adhesive temperature label 72 that an area of the thermal convection pathway 14 that was opposite to the adhesive temperature label 72 had a temperature of 95° C. to 97° C.

On the other hand, the color of the adhesive temperature label 71 was purple, indicating that an area of the thermal convection pathway 14 that was opposite to the adhesive temperature label 71 had a temperature much higher than 60° C. For cooling the first heater 31, water cooling with the use of circulated water and heat release using the heat sink 60 were compared.

In the cooling method involving water cooling, cooling was performed by inserting a silicon tube into the corresponding heater mounting hole 21 of the stage 20 and water (room temperature) was circulated therein using a peristaltic pump. The power source connected with the second heater 32 was set at a temperature of 125° C. As a result, an area of the thermal convection pathway 14 that was opposite to the heating portion 32b of the second heater 32 had a temperature of 95 to 97° C., but an area of the thermal convection pathway 14 that was opposite to the first heating portion 31b of the first heater 31 had a temperature of no greater than 57.25° C.

On the other hand, in the cooling method using the heat sink 60, the power source connected with the second heater 32 was set at a temperature of 125° C., and the heat sink 60, which included 12 heat dissipating bodies, was attached to the first heater 31. As a result, the area of the thermal convection pathway 14 that was opposite to the heating portion 32b of the second heater 32 had a temperature of 95 to 97° C., and the area of the thermal convection pathway 14 that was opposite to the first heating portion 31b of the first heater 31 had a temperature of approximately 60° C., giving an ideal temperature distribution. The thermal convection generating chip 10 was then rotated for 10 minutes with the DC power source for the motor 40 set at a voltage of 0.5 V to observe no change in the temperature distribution.

Figure 8:
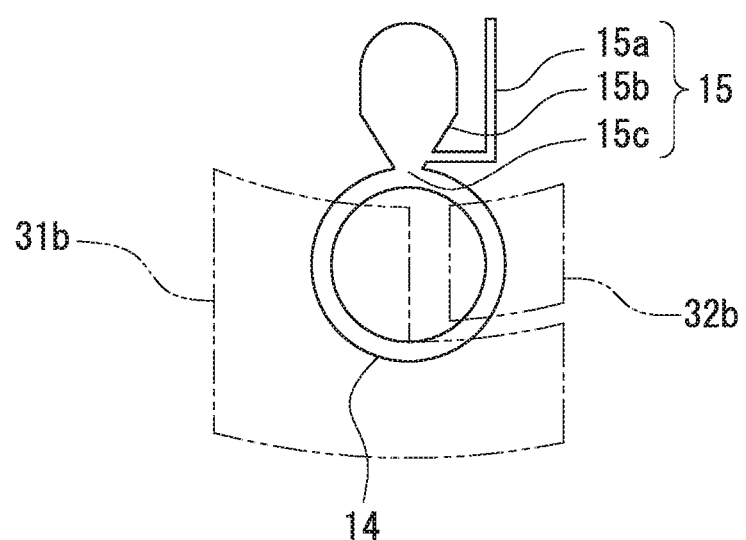
FIG. 8 is an enlarged view of a thermal convection pathway and a liquid supply path according to a second embodiment of the present invention.

Next, a second embodiment of the present invention will be described. FIG. 8 is an enlarged view of a thermal convection pathway and a liquid supply path according to the second embodiment of the present invention. Elements corresponding to elements described earlier in the first embodiment are labelled using the same reference signs and redundant description thereof is omitted.

In the present embodiment, the substrate body 12 (see FIG. 3) having the thermal convection pathways 14 and the liquid supply paths 15 is made of a complex of polydimethylsiloxane (hereinafter, referred to as "PDMS") and glass by a photolithography technique.

Each of the thermal convection pathways 14 according to the present embodiment includes a truly circular groove having an outer diameter of 6 mm, a groove width of 500 μm, and a depth of 400 μm.

An end portion of the liquid trap portion 15b of each liquid supply path 15 that is farthest from the corresponding thermal convection pathway 14 has a semicircular shape. An end portion of the liquid trap portion 15b that is closest to the thermal convection pathway 14 has an inverted triangle shape. A middle portion of the liquid trap portion 15b has a rectangular parallelepiped shape. The elongated portion 15a for introducing a liquid into the liquid trap portion 15b is L-shaped, and one end thereof is communicably connected with the inverted triangle end portion of the liquid trap portion 15b.

Other than that, the present embodiment has the same configuration as the embodiment described earlier.

In accordance with the same method as the test method described earlier, adhesive temperature labels were positioned over a heating portion 31b of the first heater 31 and a heating portion 32b of the second heater 32 to perform temperature measurement and setting of each element.

The power source for the second heater 32 was set at a temperature of 140° C., and the cooling water was set at a temperature of 50° C. As a result, the area of the corresponding thermal convection pathway 14 that was opposite to the heating portion 32b of the second heater 32 and the area of the thermal convection pathway 14 that was opposite to the heating portion 31b of the first heater 31 each had a targeted temperature. It should be noted that no heat sink was used.

A red food coloring solution was supplied to the thermal convection pathway 14 to observe whether or not air bubbles were formed. PDMS has high gas permeability and may therefore cause formation of air bubbles at high temperatures. Such air bubbles prevent liquid convection and therefore preclude heat exchange for PCR.

In the present embodiment, therefore, the thermal convection pathway 14 was filled with mineral oil in advance, and the red food coloring solution was supplied to the thermal convection pathway 14 after the PDMS had absorbed enough of mineral oil. Thereafter, the thermal convection pathway 14 was heated for 30 minutes. As a result, no air bubbles were formed. Presumably, this is because the mineral oil reduced gas permeability of the PDMS and thus prevented formation of air bubbles. The mineral oil also functions as a lid blocking the communication portion 15c.

Furthermore, the mineral oil has a boiling point higher than the heating temperature of the second heater 32, which is the maximum temperature of the heat controller 30, and therefore has an effect of inhibiting evaporation of the sample liquid. A liquid other than mineral oil may be used as the evaporation inhibitor liquid as long as the liquid has either or both of a specific gravity smaller than that of the sample liquid and a boiling point higher than the maximum temperature of the heat controller 30.

Figure 9:
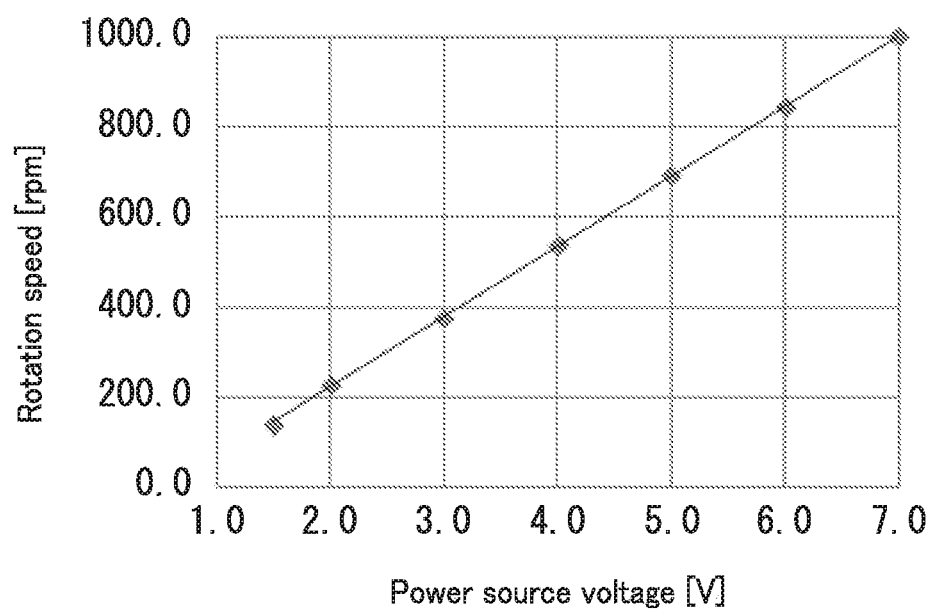
FIG. 9 is a graph illustrating a relationship between voltage of a power source for a motor and rotation speed of the motor.
Figure 10:
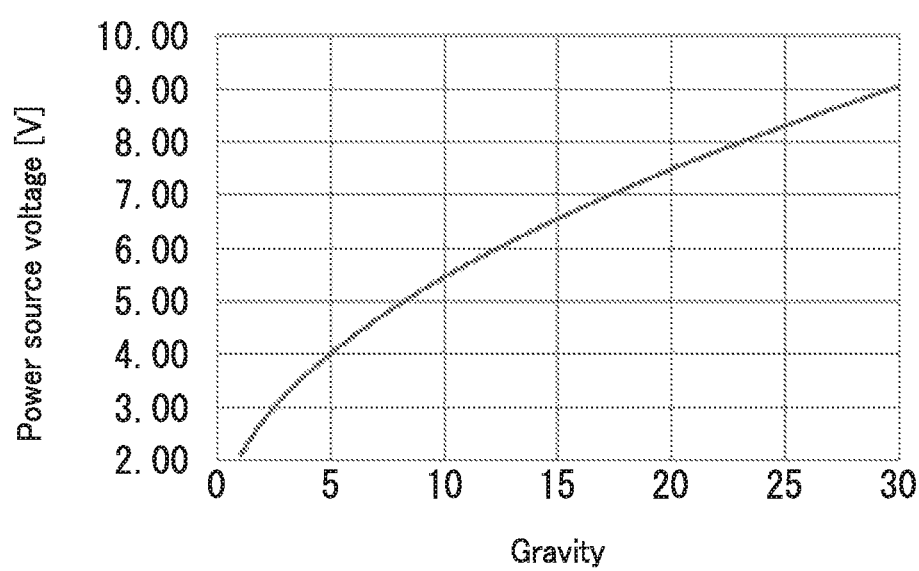
FIG. 10 is a graph illustrating a relationship between relative gravity acceleration and voltage of the power source for the motor.

FIG. 9 is a graph illustrating a relationship between voltage of the power source for the motor 40 (see FIG. 2) and rotation speed of the motor 40. FIG. 10 is a graph illustrating a relationship between relative gravity acceleration and voltage of the power source for the motor 40.

FIG. 10 was created by determining a relationship between relative gravity acceleration and rotation speed of the motor 40 in accordance with formulae that relate speed and centrifugal force ($F=mv^2/r$, $g=(2\pi N)^2 r$) and then determining the relationship between voltage and relative gravity acceleration.

The red food coloring solution and water were supplied to the thermal convection pathway 14, and the motor 40 was rotated under application of a voltage corresponding to 1G (2.12 V according to FIG. 10) with the first heater 31 and the second heater 32 energized. As a result, the liquid ran almost halfway around the thermal convection pathway 14 in 30 seconds. Converted from the result, one PCR thermal cycle is supposed to take one minute.

In the present embodiment, the liquid in the thermal convection pathway 14 takes approximately 15 seconds to pass over the corresponding heating portion 32b of the second heater 32 and takes approximately 45 seconds to pass over the corresponding heating portion 31b of the first heater 31. The times taken by the liquid to pass over the heating portion 32b and the heating portion 31b can be reduced by controlling the rotation speed of the thermal convection generating chip 10 and thus controlling the thermal convection speed.

Fluorescent PCR was performed using a β-action gene as an indicator. A PCR liquid including an amplicon as template DNA is supplied to a thermal convection pathway 14, and subsequently the motor 40 was rotated at 2.12 V for 30 minutes. Considering that thermal convection in the thermal convection pathway 14 completes one circuit in one minute, the rotation of the thermal convection pathway 14 at 1G corresponds to 30 PCR cycles.

After completion of the 30-minute rotation, fluorescence observation was performed on the thermal convection generating chip 10 to observe fluorescence associated with DNA amplification in the thermal convection pathway 14. Furthermore, the reaction solution was taken out from the thermal convection pathway 14 and electrophoresis was performed thereon to confirm that amplified products (DNA length: 289 bp) were DNA having intended lengths.

The above embodiments are described for the situations in which the thermal convection generating device 1 and the thermal convection generating chip 10 according to the present invention are used to perform thermal convection PCR. However, the thermal convection generating device 1 and the thermal convection generating chip 10 according to the present invention can be used to perform reverse transcription-PCR.

Organisms synthesize proteins through transcription of genetic sequence information from genomic DNA into RNA and translation of the genetic information from the RNA. PCR is a technique to obtain DNA molecules through amplification of a DNA molecule. In particular, reverse transcription-PCR is a PCR technique involving synthesis of DNA from RNA by the action of reverse transcriptase and the use of the DNA as a template. For example, some viruses such as influenza viruses have only RNA, having no DNA. The reverse transcription-PCR is used for confirming infection with such a virus.

The following describes a procedure for performing reverse transcription-PCR using the thermal convection generating device 1 and the thermal convection generating chip 10 according to the present invention.

As the reverse transcription-PCR, may be mentioned a method in which a reverse transcription reaction and a PCR are performed separately (two-step RT-PCR) and a method in which a reverse transcription reaction and a PCR are sequentially performed in a single liquid (one-step RT-PCR). In the present embodiment, a procedure of reverse transcription-PCR to be performed in accordance with one-step RT-PCR will be described.

As a reactant solution, for example, SuperScriptIII OneStep RT-PCR System and GeneAmp EZ rTth RNA PCR Kit, both of which are product names, produced by Life Technologies Japan Ltd.; PrimeScriptII High Fidelity One Step RT-PCR Kit and Primescript High Fidelity RT-PCR Kit, both of which are product names, produced by TAKARA BIO INC.; and the like can be used.

As a sample, for example, influenza viruses, norovirus, other general infectious disease viruses, extraction liquids from expressed RNA from cells and the like, and so forth can be used. In the case of an influenza virus, for example, a suspension of a nasal secretion or the like in an appropriate solution such as buffer solution or water can be used. In the case of norovirus, for example, a suspension of vomit or the like in an appropriate solution such as buffer solution or water can be used.

The following two methods (a) and (b) may be employed to perform reverse transcription-PCR using the thermal convection generating device 1 and the thermal convection generating chip 10 according to the present invention. The following describes the two methods (a) and (b) with reference to FIGS. 1 to 4.

(a) First, a reactant solution and a sample liquid are mixed to prepare a mixed solution. Next, the mixed solution is injected into a liquid supply path 15 of the thermal convection generating chip 10, and the thermal convection generating chip 10 is rotated to cause the mixed solution to move into the corresponding thermal convection pathway 14. Thereafter, the rotation of the thermal convection generating chip 10 is stopped, and the first heater 31 and the second heater 32 are set at the same temperature (for example, 40 to 60° C.). The mixed solution in the thermal convection pathway 14 is then heated for a specified period of time (for example, 60 seconds) to cause a reverse transcription reaction.

(b) First, a thermal convection pathway 14 of the thermal convection generating chip 10 is charged with a reactant solution, and subsequently a sample liquid is injected into a liquid supply path 15. The thermal convection generating chip 10 is rotated to cause the sample liquid in the liquid supply path 15 to move into the corresponding thermal convection pathway 14. Next, the first heater 31 and the second heater 32 are set at different temperatures to generate thermal convection of the liquids in the thermal convection pathway 14. Thus, the reactant solution and the sample liquid are mixed together to give a mixed solution. Thereafter, the rotation of the thermal convection generating chip 10 is stopped, and the first heater 31 and the second heater 32 are set at the same temperature (for example, 40 to 60° C.). The mixed solution in the thermal convection pathway 14 is then heated for a specified period of time (for example, 60 seconds) to cause a reverse transcription reaction.

Template DNA (cDNA) is synthesized from RNA through the reverse transcription reaction in accordance with the method (a) or (b) described above. Then, the first heater 31 and the second heater 32 are set at temperatures suitable for PCR (for example, the first heater 31 at a temperature of 60° C., the second heater 32 at a temperature of 95° C.) to cause a thermal convection PCR reaction.

Figure 11:
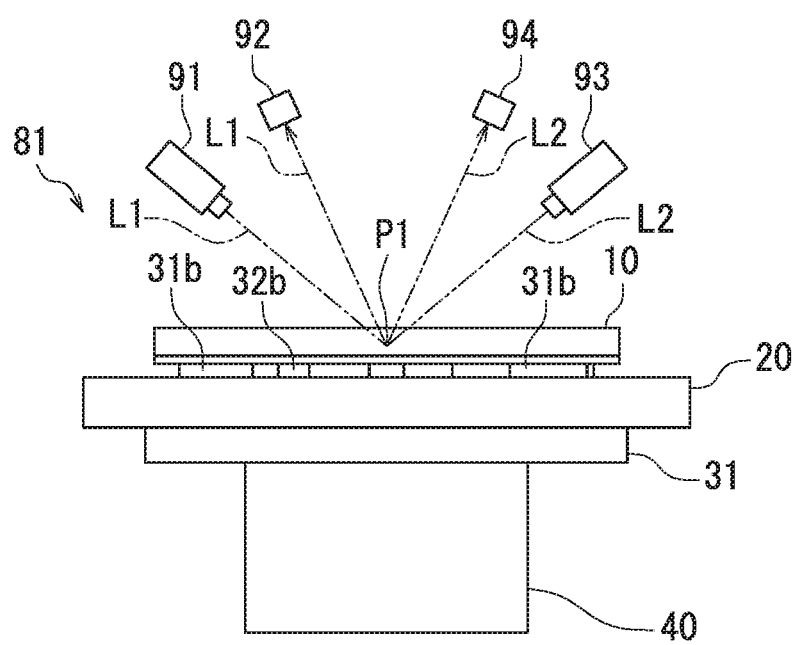
FIG. 11 is a side view of a thermal convection generating device according to a third embodiment of the present invention.
Figure 12:
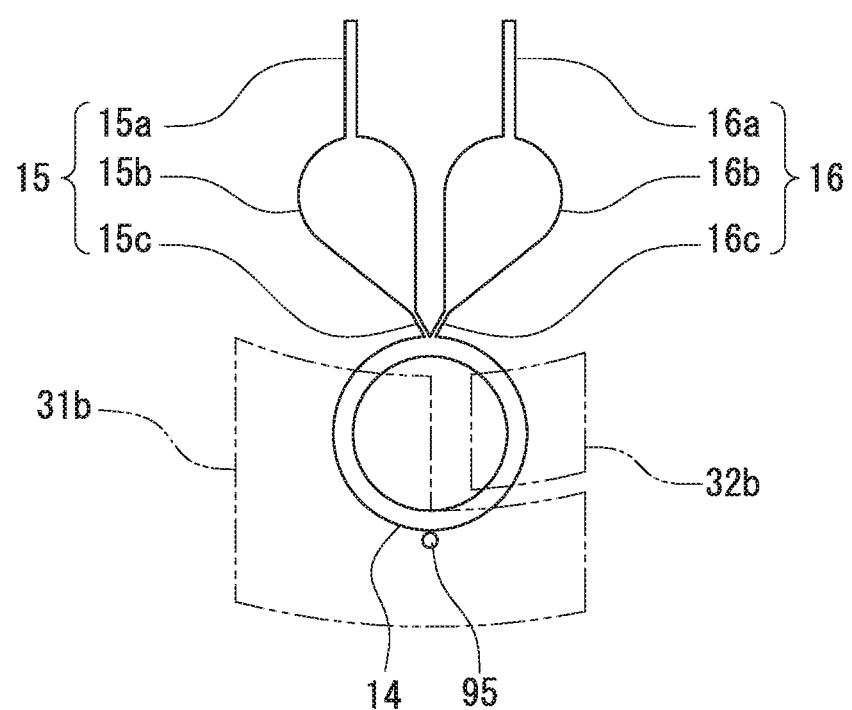
FIG. 12 is an enlarged view of a thermal convection pathway and a liquid supply path according to the third embodiment.
Figure 13:
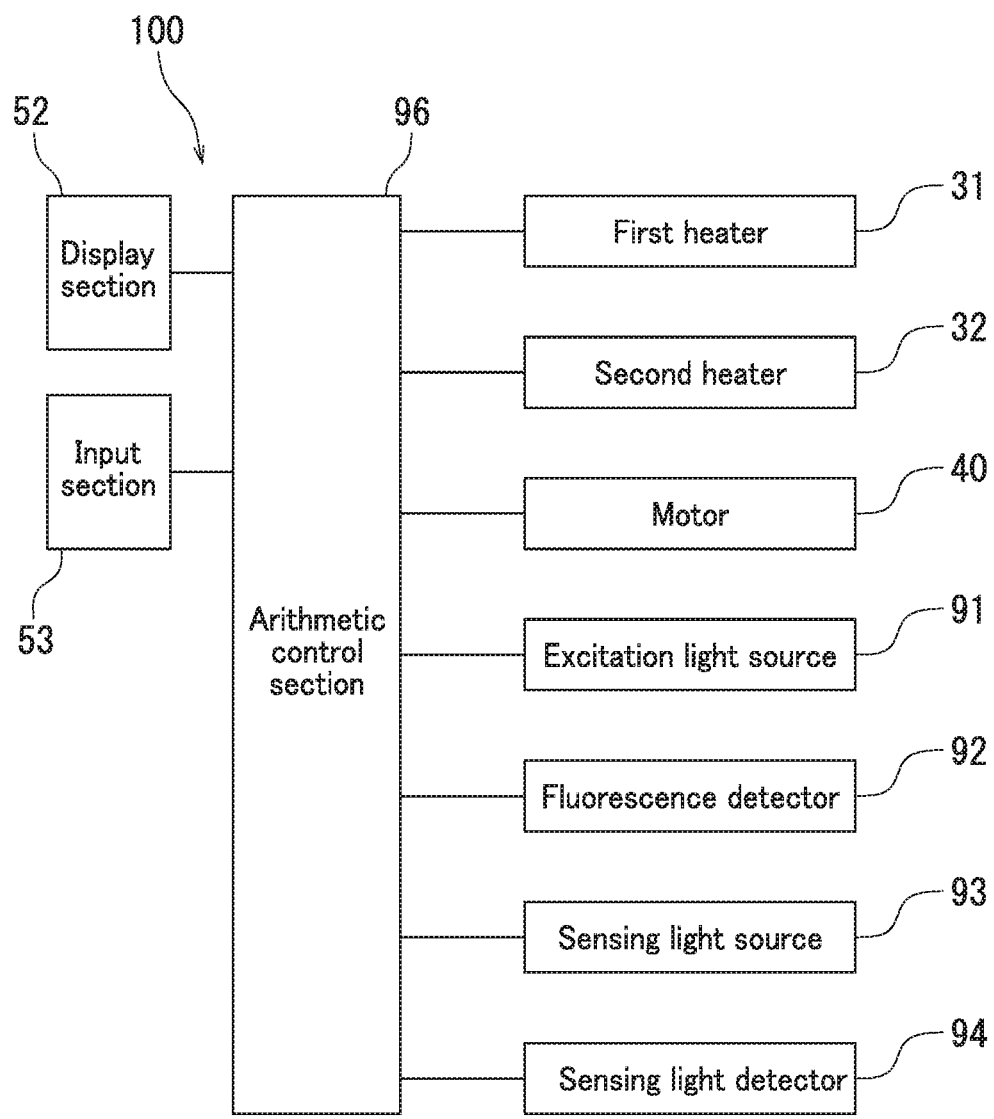
FIG. 13 is a block diagram of a control system according to the third embodiment.

Next, a third embodiment of the present invention will be described. FIG. 11 is a side view of a thermal convection generating device 81. FIG. 12 is an enlarged view of a thermal convection pathway 14 and a liquid supply path 15 according to the third embodiment. FIG. 13 is a block diagram of a control system according to the third embodiment. Elements corresponding to elements described above in the first embodiment are labelled using the same reference signs and redundant description thereof is omitted.

The thermal convection generating device 81 is capable of performing real-time PCR. The real-time PCR is a technique that enables swift quantitative determination of template DNA. In the real-time PCR, an amplification of DNA by PCR or reverse transcription-PCR is measured in real time during PCR cycles.

In the real-time PCR, PCR amplified products are detected using fluorescence. As the fluorescence detection method, an intercalator method and a hybridization method may be mentioned. The intercalator method involves the use of a fluorochrome (SYBR green I) that specifically intercalates with double-stranded DNA and emits fluorescence. The most common hybridization method is a TagMan probe method involving the use of a probe including a fluorochrome attached to an oligonucleotide specific for a DNA sequence. Examples of fluorochromes usable in the TagMan probe method include carboxyfluorescein (FAM).

As illustrated in FIG. 11, the thermal convection generating device 81 includes an excitation light source 91, a fluorescence detector 92, a sensing light source 93, and a sensing light detector 94. As illustrated in FIG. 12, a sensing light receiver 95 that reflects or scatters sensing light emitted by the sensing light source 93 is provided in the vicinity of each thermal convection pathway 14 according to the present embodiment.

As illustrated in FIG. 11, the excitation light source 91 emits light L1 toward the thermal convection pathway 14 of the thermal convection generating chip 10 while the thermal convection generating chip 10 is rotating. The light L1 is light that excites a fluorochrome contained in a liquid in the thermal convection pathway 14 (see FIG. 12) of the thermal convection generating chip 10. A laser light source can for example be used as the excitation light source 91. However, a blue light emitting diode (LED), a white light source, and the like are preferably used in terms of reduction in device cost.

The fluorescence detector 92 detects fluorescence. Fluorescence is released by the fluorochrome contained in the liquid in the thermal convection pathway 14 when the fluorochrome is irradiated with the light from the excitation light source 91. The fluorescence detector 92 for example includes a photomultiplier, a condensing lens, a fluorescence filter, and so forth.

The sensing light source 93 emits sensing light L2 (for example, laser light) toward a detection point P1 on the thermal convection generating chip 10. The detection point P1 is a fixed point set on a rotation trajectory to be formed by the sensing light receiver 95 (see FIG. 12) as a result of rotation of the thermal convection generating chip 10.

The sensing light receiver 95 reflects or scatters the sensing light emitted by the sensing light source 93. The sensing light detector 94 detects light reflected or scattered by the sensing light receiver 95. The sensing light detector 94 for example includes a photomultiplier, a condensing lens, a bandpass filter, and so forth.

FIG. 13 is a block diagram of a controller 100 that controls the thermal convection generating device 81. An arithmetic control section 96 of the controller 100 controls, as described later, the excitation light source 91 and the sensing light source 93 based on information input from the input section 53, the fluorescence detector 92, and the sensing light detector 94 as well as controls processing to be executed by the arithmetic control section 51 of the controller 50 according to the first embodiment.

The arithmetic control section 96 detects a position of the thermal convection pathway 10 during the rotational driving of the thermal convection generating chip 10 based on the reflected light or the scattered light from the sensing light receiver 95 that is detected by the sensing light detector 94. The arithmetic control section 96, the sensing light source 93, the sensing light detector 94, and the sensing light receiver 95 function as a position detector according to the present invention. Furthermore, the arithmetic control section 96 drives the excitation light source 91 based on the position of the thermal convection pathway 10 that is detected. The arithmetic control section 96 also functions as a light source controller according to the present invention.

Figure 14:
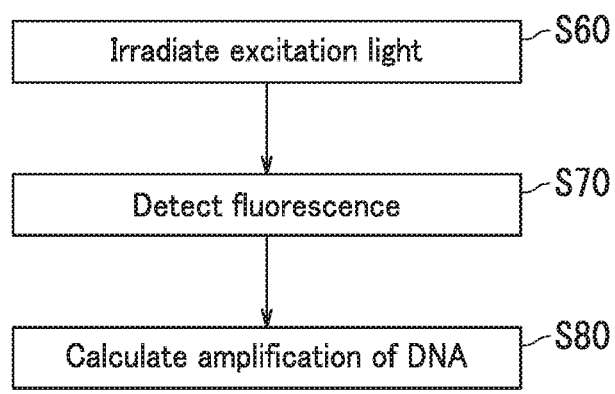
FIG. 14 is a flowchart illustrating a method for calculating an amplification of DNA using the thermal convection generating device according to the third embodiment.

The following describes a procedure for performing real-time PCR using the thermal convection generating device 81 with reference to FIGS. 11 and 14. FIG. 14 is a flowchart illustrating a method for calculating the amplification of DNA using the thermal convection generating device 81.

Upon information instructing initiation of real-time PCR being input into the arithmetic control section 96 through the input section 53 of the controller 100 (see FIG. 13), the motor 40 is driven, and the first heater 31 and the second heater 32 are energized. As a result, the thermal convection generating chip 10 rotates, and a liquid in the thermal convection pathway 14 (see FIG. 12) is heated, so that thermal convection of the liquid in the thermal convection pathway 14 is started. Thus, PCR is started.

In the present embodiment, the amplification of DNA is calculated in a thermal convection promotion step (Step S40 and Step S50 in FIG. 6). Specifically, the sensing light source 93 starts emitting sensing light to the detection point P1 at the same time that the thermal convection generating chip 10 starts rotating. The sensing light receiver 95 (see FIG. 12) provided on the thermal convection pathway 14 of the thermal convection generating chip 10 reflects or scatters the sensing light from the sensing light source 93 as the sensing light receiver 95 passes the detection point P1.

Upon the sensing light detector 94 detecting the sensing light reflected or scattered by the sensing light receiver 95, the excitation light source 91 emits excitation light to a region of the thermal convection pathway 14 that is in the vicinity of the detection point P1 as shown in Step S60 in FIG. 14. Step S60 corresponds to an excitation light irradiation step according to the present invention. The excitation light is irradiated onto the mixed solution in the thermal convection pathway 14, and fluorescence emitted by a fluorochrome molecule in the mixed solution is detected by the fluorescence detector 92 as shown in Step S70. Step S70 corresponds to a fluorescence detection step according to the present invention.

Next, as shown in Step S80, the arithmetic control section 96 calculates the amplification of DNA based on the fluorescence detected by the fluorescence detector 92. Step S80 corresponds to a DNA amplification calculation step according to the present invention. Next, quantitative determination of template DNA is made based on the amplification. The above-described real-time PCR is performed on all the thermal convection pathways 14 of the thermal convection generating chip 10.

Figure 15:
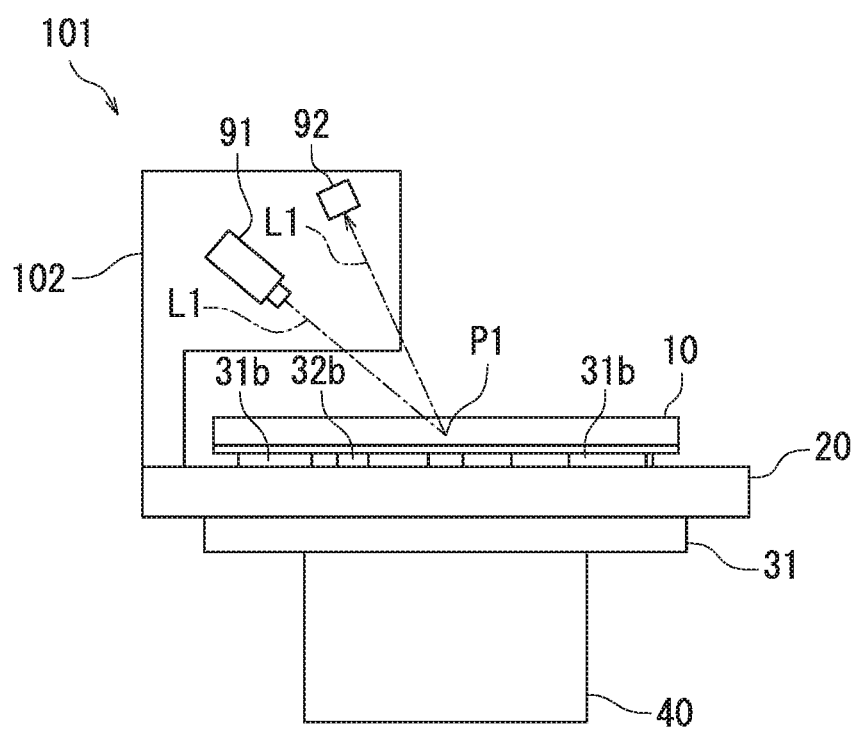
FIG. 15 is a side view of a thermal convection generating device according to a fourth embodiment of the present invention.

Next, a fourth embodiment of the present invention will be described. FIG. 15 is a side view of a thermal convection generating device 101 according to the third embodiment. Elements corresponding to elements described above in the third embodiment are labelled using the same reference signs and redundant description thereof is omitted.

In the present embodiment, the excitation light source 91 and the fluorescence detector 92 are supported on a supporting member 102 fixed to the stage 20, and the excitation light source 91 and the fluorescence detector 92 rotate integrally with the thermal convection generating chip 10. Furthermore, the present embodiment does not include the sensing light source 93, the sensing light detector 94, or the sensing light receiver 95 according to the third embodiment. Other than that, the present embodiment has the same configuration as the third embodiment.

According to the present embodiment, excitation light can be irradiated onto a liquid in each thermal convection pathway 14 more reliably compared to the configuration in which the excitation light source 91 and the fluorescence detector 92 do not rotate integrally with the thermal convection generating chip 10. Thus, the present embodiment has an effect of improving the accuracy of the fluorescence detection. Furthermore, the manufacturing cost of the present embodiment is lower because the sensing light source 93, the sensing light detector 94, and the sensing light receiver 95 according to the third embodiment are not necessary.

Specific embodiments of the present invention are described above. However, the present invention is not limited to the above-described embodiments and alterations can be made to the embodiments within the scope without departing from the scope of the present invention.

For example, although the heat controller 30 is provided separately from the thermal convection generating chip 10 in the embodiments described above, the heat controller 30 may be provided in the thermal convection generating chip 10. In such a configuration, for example, a wire heater or the like, which is space-saving and light-weight, can be used as the heat controller.

Furthermore, the present invention is applicable to devices that perform processes other than thermal convection PCR and reverse transcription-PCR.

Furthermore, although the above embodiments are described for the configuration in which the thermal convection generating device includes two heat controllers, the thermal convection generating device may include one heat controller or three or more heat controllers.

Furthermore, although the thermal convection generating chip according to the above-described embodiments has a disk-like shape, the thermal convection generating chip may not have a disk-like shape.

Furthermore, although each of the thermal convection pathways according to the above-described embodiments has one liquid supply path, each of the thermal convection pathways may have a plurality of liquid supply paths.

Furthermore, although each of the thermal convection pathways according to the above-described embodiments has one gas discharging path, each of the thermal convection pathways may have a plurality of gas discharging paths.

Other than those described above, various alterations can be made to the embodiments within the scope without departing from the scope of the present invention.

REFERENCE SIGNS LIST

1 Thermal convection generating device
10 Thermal convection generating chip
14 Thermal convection pathway
15 Liquid supply path
16 Gas discharging path
20 Stage (chip mounting section)
30 Heat controller
31 First heater (low temperature heat controller)
31b Heating portion
32 Second heater (high temperature heat controller)
32b Heating portion
40 Motor (driver)
50 Controller
60 Heat sink (heat dissipator)
91 Excitation light source
92 Fluorescence detector
93 Sensing light source (position detector)
94 Sensing light detector (position detector)
95 Sensing light receiver (position detector)
96 Arithmetic control section (position detector, light source controller)
100 Controller
S Gap
E1 Low temperature area
E2 Gap area
E3 High temperature area

The invention claimed is:

1. A thermal convection generating chip comprising:
a substrate;
at least one annular thermal convection pathway provided in the substrate, the annular thermal convection pathway having an inside circumferential surface and an outside circumferential surface;
at least one liquid supply path that is provided in the substrate, that is connected to the outside circumferential surface of the annular thermal convection pathway, and through which a liquid is supplied into the annular thermal convection pathway; and
at least one gas discharging path that is provided in the substrate, that is connected to the outside circumferential surface of the annular thermal convection pathway, and that is configured to receive gas in a liquid in the annular thermal convection pathway,
wherein the thermal convection generating chip has a rotation axis and is configured to rotate to apply centrifugal force to a liquid in the annular thermal convection pathway,
the liquid supply path and the gas discharging path are arranged in a symmetric manner with respect to the annular thermal convection pathway,
the liquid supply path includes a first portion connected to the annular thermal convection pathway, a second portion connected to the first portion, and a third portion connected to the second portion, the second portion having a width larger than a width of the first portion, the third portion having a width smaller than the width of the second portion,
the at least one annular thermal convection pathway includes a plurality of annular thermal convection pathways that are rotatable about the rotation axis, and
the annular thermal convection pathways are arranged in a symmetric manner with respect to the rotation axis.

2. The thermal convection generating chip according to claim 1, wherein
the thermal convection generating chip is configured to rotate to apply centrifugal force to a liquid in the liquid supply path to cause the liquid to move into the annular thermal convection pathways.

3. The thermal convection generating chip according to claim 1, wherein
each of the annular thermal convection pathways has a wall with a surface roughness Ra of no greater than 100 nm.

4. The thermal convection generating chip according to claim 1, wherein
the gas discharging path includes a first portion connected to the annular thermal convection pathways, a second portion connected to the first portion, and a third portion connected to the second portion, the second portion having a width larger than that of the first portion, the third portion having a width smaller than that of the second portion.

5. The thermal convection generating chip according to claim 1, wherein
the substrate has a main surface, and
the width of the first portion, the width of the second portion, and the width of the third portion each are a width in a direction along the main surface of the substrate.

6. The thermal convection generating chip according to claim 1, wherein
the second portion has a capacity larger than the annular thermal convection pathways.

7. The thermal convection generating chip according to claim 1, wherein
each of the annular thermal convection pathways has a truly circular shape.

8. The thermal convection generating chip according to claim 1, wherein
each of the annular thermal convection pathways has a section that is located closest to the rotation axis of the thermal convection generating chip and that is communicably connected with the at least one liquid supply path and the at least one gas discharging path in a bifurcated and symmetrical manner.

9. A thermal convection generating device comprising:
a chip mounting section including the thermal convention generating chip according to claim 1 attached thereto;
a heat controller configured to heat or cool a portion of each of the annular thermal convection pathways; and
a driver configured to rotationally drive the thermal convection generating chip.

10. The thermal convection generating device according to claim 9, wherein
the heat controller includes a low temperature heat controller and a high temperature heat controller,
a difference in temperature between a heating portion of the low temperature heat controller and a heating portion of the high temperature heat controller is no less than 10° C.,
a difference in temperature between the heating portion of the low temperature heat controller and a gap between the heating portion of the low temperature heat controller and the heating portion of the high temperature heat controller is no less than 10° C., and
a difference in temperature between the gap and the heating portion of the high temperature heat controller is no less than 10° C.

11. The thermal convection generating device according to claim 9, wherein an area of each of the annular thermal convection pathways that is opposite to the heat controller has a temperature higher or lower than an area of each of the annular thermal convection pathways other than the area opposite to the heat controller.

12. The thermal convection generating device according to claim 9, further comprising
a controller configured to control a temperature of the heat controller for heating or cooling the annular thermal convection pathways, and a speed and a time of the rotational driving of the thermal convection generating chip by the driver.

13. The thermal convection generating device according to claim 9, wherein
the thermal convection generating device is adapted to perform thermal convection PCR in the annular thermal convection pathways.

14. The thermal convection generating device according to claim 13, comprising:
an excitation light source configured to irradiate the liquid to which the centrifugal force is applied in the annular thermal convection pathways with excitation light that excites a fluorochrome contained in the liquid to which the centrifugal force is applied in the annular thermal convection pathways;
a fluorescence detector configured to detect fluorescence emitted by the fluorochrome upon irradiation with the excitation light; and
an arithmetic control section configured to calculate an amplification of DNA based on the fluorescence detected by the fluorescence detector.

15. The thermal convection generating device according to claim 14, further comprising:
a position detector configured to detect a position of each of the annular thermal convection pathways during the rotational driving of the thermal convection generating chip; and
a light source controller configured to drive the excitation light source based on a result of the detection by the position detector.

16. The thermal convection generating device according to claim 14, wherein
the excitation light source and the fluorescence detector rotate integrally with the thermal convection generating chip.

17. A thermal convection generation method comprising:
a chip preparation step of preparing the thermal convection generating chip according to claim 1;
a liquid supply step of supplying the liquid supplied through the liquid supply path into the annular thermal convection pathways; and
a thermal convection promotion step of heating or cooling a portion of each of the annular thermal convection pathways while rotationally driving the thermal convection generating chip to apply centrifugal force to the liquid.

18. The thermal convection generation method according to claim 17, wherein
the liquid includes an evaporation inhibitor liquid having either or both of a boiling point higher than a maximum temperature of a heat controller configured to heat the liquid and a specific gravity smaller than that of the liquid.

19. The thermal convection generation method according to claim 17, wherein
the thermal convection generation method is adapted to perform thermal convection PCR in the annular thermal convection pathways.

20. The thermal convection generation method according to claim 19, wherein
the liquid in the annular thermal convection pathways includes a fluorochrome, and
the thermal convection promotion step includes:
an excitation light irradiation step of irradiating the liquid in the annular thermal convection pathways with excitation light that excites the fluorochrome;
a fluorescence detection step of detecting fluorescence emitted by the fluorochrome upon irradiation with the excitation light; and
a DNA amplification calculation step of calculating an amplification of DNA based on the detected fluorescence.

* * * * *